United States Patent [19]

Blackmer et al.

[11] Patent Number: 4,955,372
[45] Date of Patent: Sep. 11, 1990

[54] METHOD AND APPARATUS FOR PULMONARY AND CARDIOVASCULAR CONDITIONING OF RACEHORSES AND COMPETITION ANIMALS

[75] Inventors: Richard H. Blackmer, Scotia; Jonathan W. Hedman, Burnt Hills, both of N.Y.

[73] Assignee: Transpirator Technologies, Inc., Somerset, N.J.

[21] Appl. No.: 436,085

[22] Filed: Nov. 13, 1989

Related U.S. Application Data

[63] Continuation of Ser. No. 841,300, Mar. 19, 1986, abandoned, which is a continuation-in-part of Ser. No. 755,562, Jul. 16, 1985, Pat. No. 4,722,334.

[51] Int. Cl.⁵ .............................................. A61M 15/00
[52] U.S. Cl. .......................... 128/203.16; 128/203.17; 128/203.26; 128/203.27; 128/204.17
[58] Field of Search ...................... 128/200.14, 200.16, 128/200.18, 200.21, 203.16, 203.17, 203.26, 203.27, 204.17

[56] References Cited

U.S. PATENT DOCUMENTS

| | | | |
|---|---|---|---|
| 2,091,034 | 8/1937 | Duncan | 128/203.27 |
| 2,843,119 | 7/1958 | Glasser | 128/206.26 |
| 3,379,194 | 4/1968 | Ziermann | 128/200.21 |
| 3,638,926 | 2/1972 | Melville et al. | 128/203.27 |
| 3,863,630 | 2/1975 | Cavallo | 128/203.27 |
| 3,873,806 | 3/1975 | Schosson | 128/203.27 |
| 4,038,980 | 8/1977 | Foder | 128/203.27 |
| 4,060,576 | 11/1977 | Grant | 128/203.27 |
| 4,201,204 | 5/1980 | Rinne et al. | 128/203.27 |
| 4,314,138 | 2/1982 | Itoh | 128/203.27 |
| 4,319,566 | 3/1982 | Hayward et al. | 128/203.26 |
| 4,369,777 | 1/1983 | Lwoff et al. | 128/200.14 |
| 4,381,267 | 4/1983 | Jackson | 261/104 |
| 4,401,114 | 8/1983 | Lwoff et al. | 128/200.14 |
| 4,564,748 | 1/1986 | Gupton | 128/203.27 |
| 4,722,334 | 2/1988 | Blackmer et al. | 128/204.17 |

OTHER PUBLICATIONS

Heller, Bill, "New Hope for Horses with Breathing and Bleeding Problems", *HoofBeats*, Dec. 1985.
Killay, Emily, "Drug Tests and Hot Air Offer Hope for Respiratory Relief", Equus. Magazine; vol. 104, Jun. 1986.
Pines, Phillip, "Hot to Trot", *Sports Eye Magazine*, vol. 23, #107, May 1986.
Weeks, Helma, "EIPH in Racehorses", *The Backstrength*, Jul. 1986.
Strassburger, John; "Kulak Chases Her Dream with Cobblestone", Chronicle of the Horse; vol. XLIX, No. 1, Jan. 3, 1986.
Sweeny, Corinne, "Exercised Induced Pulmonary Hemorrhage", Current Therapy in Equine Medicine-2 W. B. Saunders, Co. Phila, 1987.
Biles, Deirdre, "Hot Air and Horses", *The Blood Horse*, Mar. 15, 1986.
Clippenger, Don, "Hot Air to Help Horses Performance, Professor Reports", The Philadelphia Inquirer, Feb. 21, 1986.
Skramstad, Sherry, "Drugs in Racing, Part II: Lasix", *Hub Rail Magazine*, Nov.-Dec. 1986.
Beech, Jill, "New Topics in Respiratory Therapy", Present.of Amer. Assc. Equine Pract., 32 Annual Conf., Nashville, Tenn. Dec. 1986.
Lieberman, Bobbie, "Is Hot and Humid a Breath of Fresh Air?" Modern Horse Breeding; vol. 3, #7, Jul. 1986.
Thomas, Heather, "Bleeders: Why They Bleed and How You Can Help Prevent It", Hub Rail Magazine, Sep.-Oct. 1986.
Transpirator Technologies Inc. Product Liter., "Drug-Free Therapy for Bleeding and Other Respiratory Disorders".

Primary Examiner—Randall L. Green
Assistant Examiner—K. M. Reichle
Attorney, Agent, or Firm—Kane, Dalsimer, Sullivan, Kurucz, Levy, Eisele and Richard

[57] ABSTRACT

A method and apparatus for delivering a humidified stream of gas to an animal's respiratory tract. The gas is delivered at a dew point temperature greater than the ambient dew point temperature.

23 Claims, 5 Drawing Sheets

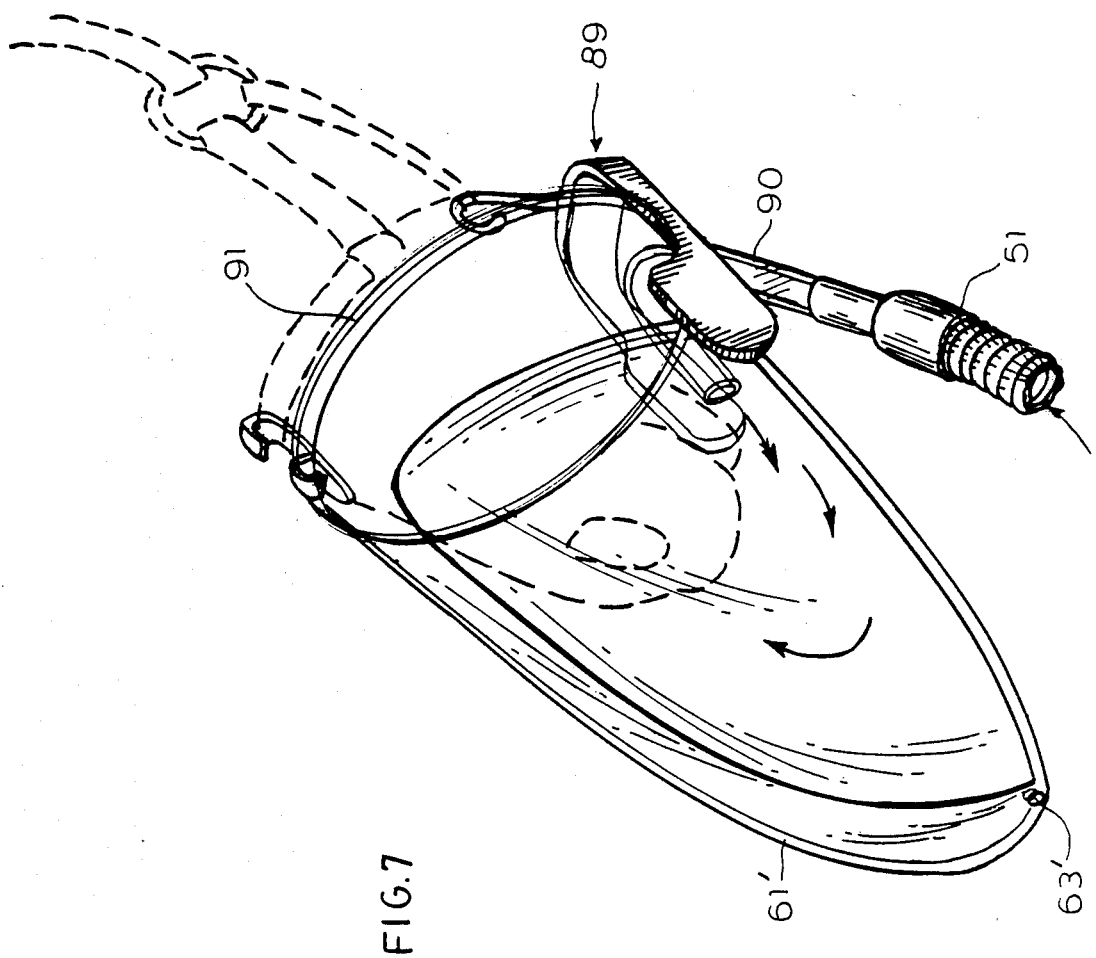

METHOD AND APPARATUS FOR PULMONARY AND CARDIOVASCULAR CONDITIONING OF RACEHORSES AND COMPETITION ANIMALS

BACKGROUND OF THE INVENTION

CROSS-REFERENCE TO RELATED APPLICATIONS

This is a continuation of application Ser. No. 841,300, filed on 3/19/86, now abandoned, and that application is a continuation-in-part of U.S. patent application No. 755,562, filed Jul. 16, 1985, now U.S. Pat. No. 4,722,334 The invention of the present application improves upon the invention of U.S. patent application No. 755,562 in that it provides an apparatus with a much faster heat up time and at the same time is simpler in design and less expensive. The apparatus of the present invention also contains numerous safety features which will become obvious.

FIELD OF THE INVENTION

A high-humidity method and an apparatus are described which are useful for conditioning the respiratory pulmonary and/or a cardiovascular system in an animal. More particularly a method and an apparatus which are useful for delivering a therapeutic stream of humidified gas to an animal's respiratory tract at a dew point temperature greater than the ambient dew point temperature.

DESCRIPTION OF THE PRIOR ART

The treatment of the respiratory tract of large animals with heated, humidified air is virtually unreported in both patent and technical journal literature. Large animals is a term commonly used in the art to refer to the following animals: equine, including standardbred and thoroughbred horses, bovine, and ovine species.

Respiratory therapy involving conditioning of the pulmonary and/or cardiovascular systems of large animals comprising delivering a saturated vapor/gas stream at a dew point temperature greater than the environmental ambient dew point temperature has not been proposed in the prior art or reported in the literature.

Inhalation therapy involving inhalation by large animals of water-vapor-saturated air at dew point temperatures above ambient to above 110° F. while administering 300 to 400 liters per minute of such air to standardbred and thoroughbred racehorses also has not been found in technical literature.

In general, prior patent and technical art refer to the administration of medicines, anesthesia, drugs, (M.A.D.), etc., to small animals such as cats, dogs, chickens and the like for the purpose of enhancing vaccinations, etc. Water vapor reportedly has been transferred into the respiratory system of small animals at temperatures equal to or lower than the normal body temperature of the animals. Therapy treatment (i.e., other than replacement of bypassed natural humidification anesthesia or other procedures involving tracheal intubation) of the respiratory tract of animals at dew point temperatures near or above normal core body temperatures is, unreported or unsuggested in the prior art.

The present invention is a drug free therapeutic treatment for respiratory disease in animals. Respiratory disease is second only to bone and muscle problems in limiting a race horse's ability to perform. Improving a horse's pulmonary function by removing airway obstructions reduces the work of breathing and improves oxygenation; two major factors in allowing the equine athlete to race to his full potential. Improving mucocilliary clearance can lead to shorter recovery times for horses with respiratory complications, getting the animal back on the track faster for training and racing.

SUMMARY OF THE INVENTION

A high humidity method and an apparatus for therapeutic of animals are described which are useful for conditioning respiratory, pulmonary and/or a cardiovascular system in an animal. The method broadly comprises delivering a humidified stream of gas at a dew point temperature greater than the ambient dew point temperature to an animal's respiratory tract. This reduces airway water loss and upon cooling produces a thin film of condensation on the walls of the entire respiratory tract from the nasal sinus to the alveoli. Retained and absorbed water thins the mucous blanket, dissolves mucous plugs, and promotes mucocilliary clearance.

A high-humidity therapy and apparatus are described which are useful for clearing pulmonary secretions and hydrating the pulmonary tract and for increasing peripheral blood circulation before exercise of large competition animals.

The invention is particularly useful for the prevention and treatment of exercise-induced pulmonary hemorrhage (EIPH) in racehorses. More specifically, the invention relates to apparatus and methods where the humidity level in the respiratory tracts of large animals is increased by muzzle mask administration of water-vapor saturated air to produce inspired dew point temperatures above ambient up to about 110° F. and no higher than 115° F. When the respiratory tracts of animals are preconditioned and/or treated with vapor-phase water, tissue damage from EIPH is avoided or reduced in one or more of the following areas: the bronchi, bronchioles, alveolar ducts/sacs, arterial and venous capillaries, and other areas of the respiratory system. The therapy treatment described herein reduces evaporative cooling in the respiratory system and thereby promotes compensatory peripheral blood circulation with a minimum consumption of energy reserves.

The pathophysiology of exercise-induced pulmonary hemorrhage is believed to involve rupture and tearing of alveolar blood capillaries caused by negative air pressure and by over-expansion of unobstructed alveoli during maximum inspiratory effort. The present invention is a method to minimize negative inspiratory pressure and obstruction of bronchial connections to the alveoli by promoting the natural mucocilliary secretion and particulate-clearance action of the bronchial system by the prevention of airway water loss and by the hydration of airway surfaces through the administration to the upper respiratory tract of large animals of a substantially sterile, water-vapor-saturated airstream. This method of improving pulmonary hygiene helps condition the animal to achieve its maximum oxygenation efficiency through reduction of airway obstructions and hydration of airway membranes and mucous. The method also eliminates evaporative cooling from the respiratory system and, typically will increase metabolic heat rejection from other body surfaces by about 10 percent, and consequently, induces increased peripheral blood circulation.

Thus, the method of this invention not only conditions the pulmonary system but also serves as a pre-exercise warmup method to reduce exercise warmup and thereby save energy reserves for the race.

The veterinary respiratory therapy apparatus of the present invention is particularly adapted for application of vapor-phase water in treating the upper respiratory tract of large animals with a substantially sterile, water-vapor-saturated airstream having a substantially uniform dew point/dry bulb temperature above ambient temperature and to above 110° F. and at flow rates between 60 (or lower) and 500 (or higher) liters per minute, sufficient to match the normal peak inhalation flow rate of a typical racehorse.

The apparatus of the invention comprises a portable electric-powered air blower, means for humidifying the air stream, a flexible delivery tube, means for conducting the humidified air without excessive condensation to a muzzle mask and means for administering the humidified air to the nasal passages of a large animal such that the dew point temperature of the inspired air can be controlled from above ambient to above 110° F. The unified apparatus comprises elements that are relatively inexpensive, portable, and can be operated or maintained by individuals not having a high degree of technical expertise or horse-handling skill for pulmonary and cardiovascular conditioning of racehorses and other large animals.

BRIEF DESCRIPTION OF THE DRAWINGS

FIG. 7 is a perspective view of a muzzle made for the administration of a high humidity air stream to a equine.

DETAILED DESCRIPTION OF THE PREFERRED EMBODIMENTS

Figure 1:
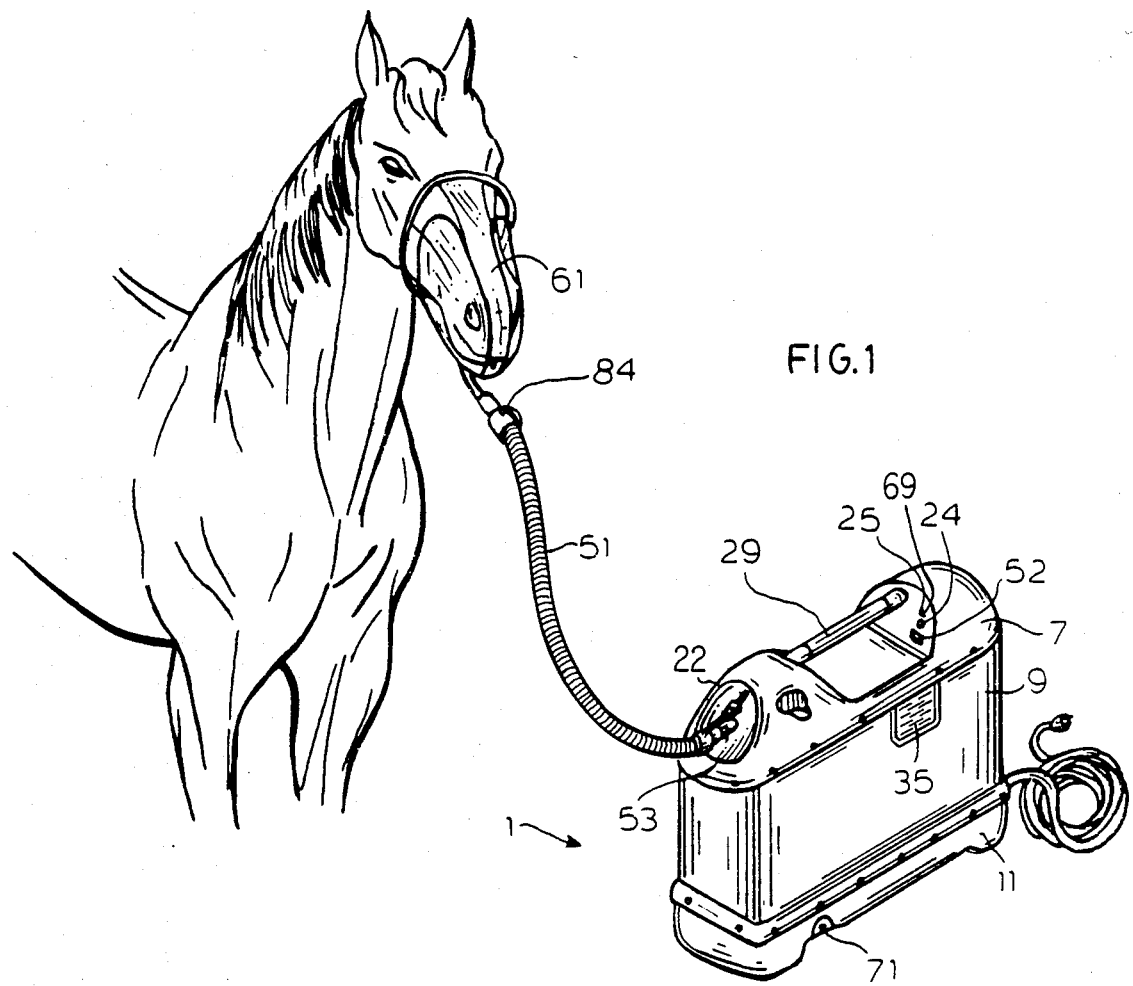
FIG. 1 is a front oblique perspective view of the right side of the portable electric powered humidifier unit showing the muzzle mask secured for the administration of a high-humidity air stream to an equine.

FIG. 1 is a front oblique perspective view of the right side of the portable electric powered humidifier unit showing the muzzle mask secured for the administration of a high-humidity air stream to an equine. Ambient air enters the cabinet 1 at atmospheric pressure, through air filter 35, exits into a delivery tube 51 after mixing with moisture laden air, and is delivered to the animal standing on the left side of the cabinet via a muzzle mask.

Although the apparatus as shown is designed for ambient air, it can be readily adapted to receive gas under pressure. Oxygen, nitrous oxide, and other inhaled anesthetic and therapeutic agents can be used.

Figure 4:
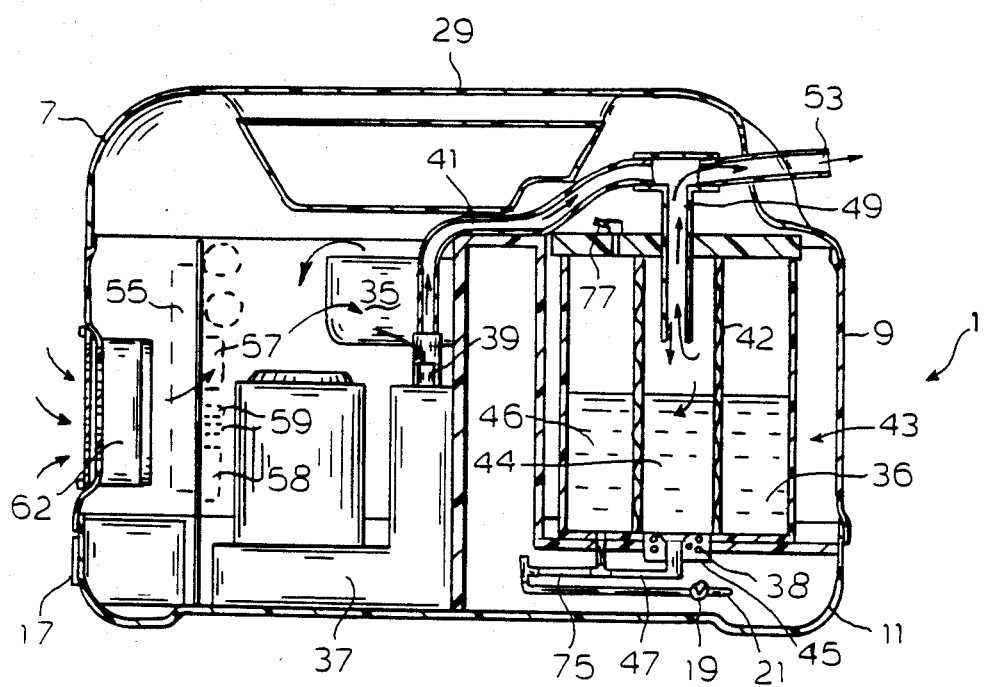
FIG. 4 is a vertical cut-away showing air flow through the right half of the apparatus.

Referring now to FIG. 4, the air enters the cabinet through air filter 35 and is drawn into the gas blower 37 through intake orifice 39 and exits via a plastic conduit 41 under positive pressure. The air mixes with moisture laden air rising through a second conduit 49 and exits the heating container 43. The air flows mix at the intersection of the two conduits 41 and 49 and then continues through a third plastic conduit 53, exits the cabinet 1 and flows through the plastic delivery tube 51 into the mask 61.

Figure 5:
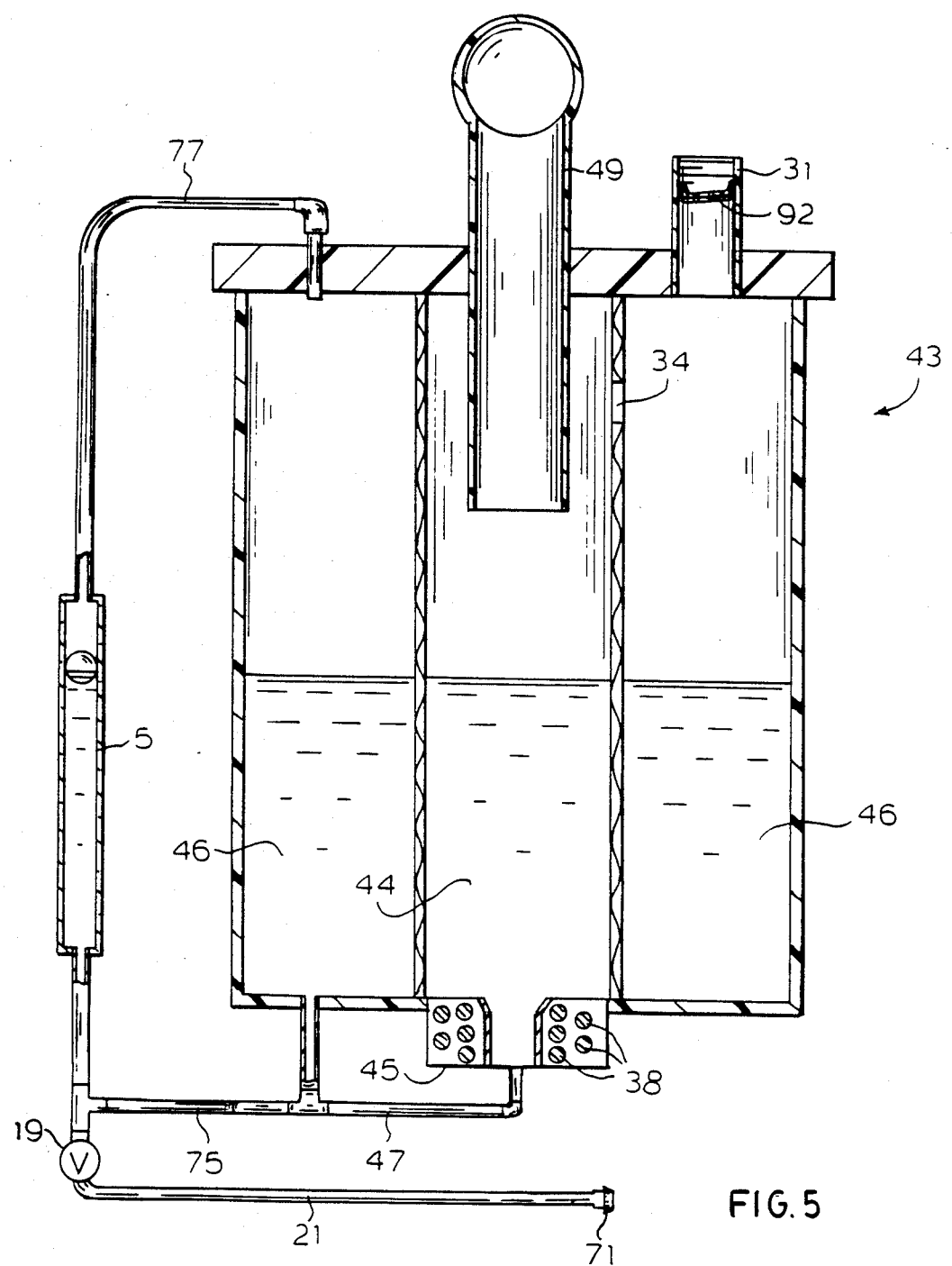
FIG. 5 is a sectional view of the humidification pot.

Referring now to FIG. 5, water enters the cabinet 1 from a liquid inlet port 31 into the outer reservoir 46 of the insulated stainless steel heating container 43. A plastic tube 42 divides the container into an inner reservoir 44 and an outer reservoir 46. Water flows into the inner reservoir 44 through tubing 47 until the fluid levels in the two reservoirs are equal. A vent 34 near the top of the divider 42 allows the air pressure into the two chambers to equilibrate.

Water in the inner chamber is in direct contact with an electric heater 45. When the invention is switched on, electric power is fed to the heater coils 38 which are embedded in the electric heater. Water in the inner reservoir 44 is preferentially heated. The water sequestered in the inner reservoir 44 is a minor portion of the water in the container 43 and permits a fast heat up.

The electric heater 45 imparts sufficient energy to the water 36 in the interior chamber to humidify the air in the chamber. Hot moisture laden air flows into conduit 49 and then mixes with the ambient air flow and is delivered to the animal.

The conduit 49 is axially aligned with the plastic tube 42. This minimizes the effect of tilting of the cabinet 1 on the water level and also enhances the vapors ability to enter the conduit 49.

Water within the inner reservoir 44 is heated by the electric heater 45 to boiling temperature in excess of the temperature required for pasteurization, i.e., 140° to 180° F. Pasteurizing the water serves to stop the spread of bacterial contaminants which are a source of respiratory infections. Pathogenic organism can multiply in the unheated container 43 but will be pasteurized as they pass from chamber 46 to chamber 44 where the water is vaporized for introduction into the air on its way to the animals respiratory tract.

The delivery tube 51 is heated by the water vapor. Insulation may be added to minimize condensation of water vapor on cooling. The delivery tube may be optionally heated by electrical or water-jacket means to prevent condensation.

The electric heater 45 administers heat to the interior chamber in response to control signals from a wet-bulb temperature sensor 84 (shown in FIG. 1) located near the exit of delivery tube 51. Should the temperature at the sensor 84 exceed a pre-determined upper limit, i.e., 115° F., a thermal switch opens thereby turning off power to the electric heater 45.

In the event that the sensor is disconnected and no temperature measurement can be made, the power to the heater 45 will be turned off. However, the fan and the blower will still operate. Thus, the disconnected sensor 84 will send unheated ambient air through the delivery tube. This air will have an additional water carrying capacity and can be used to dry the delivery tube. During such procedures, the muzzle mask is not to be connected to an animal.

A recessed liquid drain outlet port 71 (shown in FIG. 1) and drain valve 19 (shown in FIG. 5) are incorporated to provide a means of removing water from the container 43. To drain the water, a recessed drain lever 73 located on the left side of the cabinet (shown in FIG.

2) is rotated to open drain valve 19. Gravity forces the water through drain conduit via outlet port 71. Conduit 21 is beneath the heating container 43 and delivers the water to the elevated drain port 71 on the right side of the cabinet away from the animal. This design is a safety feature which prevents water from spilling on the animal or on the attendant who opens the valve.

A sight tubing 5 (shown in FIG. 2) on the left side of the cabinet permits the user to check the water level in the heating container 43 prior to starting treatment. The sight tubing is operationally connected to the water reservoir via a conduit 75 (shown in FIG. 5). A conduit 77 permits the air pressure in the sight tube 5 and the heating container to equilibrate.

In normal operation, water in the inner reservoir 44 acts as a heat sink to keep the temperature of heater 45 below a predetermined level. When the reservoirs 44 and 46 run dry the temperature of the electric heater 45 increases. A sensor 79 (not shown) attached to the electric heater automatically shut the power to the heater off when it exceeds a predetermined temperature. An indicator light marked "Refill" located on the control panel 69 will lock on.

Figure 6A:
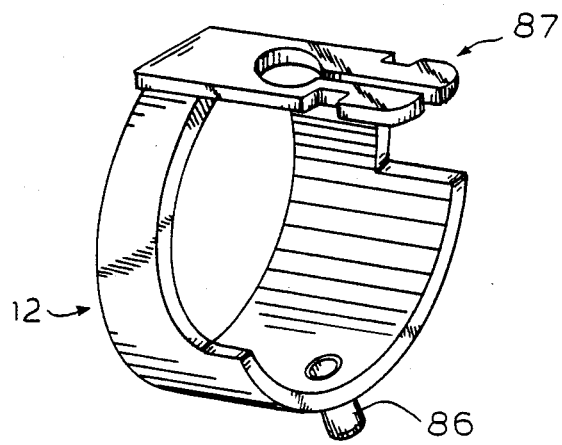
FIG. 6A is a perspective view of the muzzle mask diffuser.

FIG. 6A depicts a muzzle mask diffuser 12 with latching retainer 87 and pin 86, whose function will be described more fully in the following paragraph.

Figure 6B:
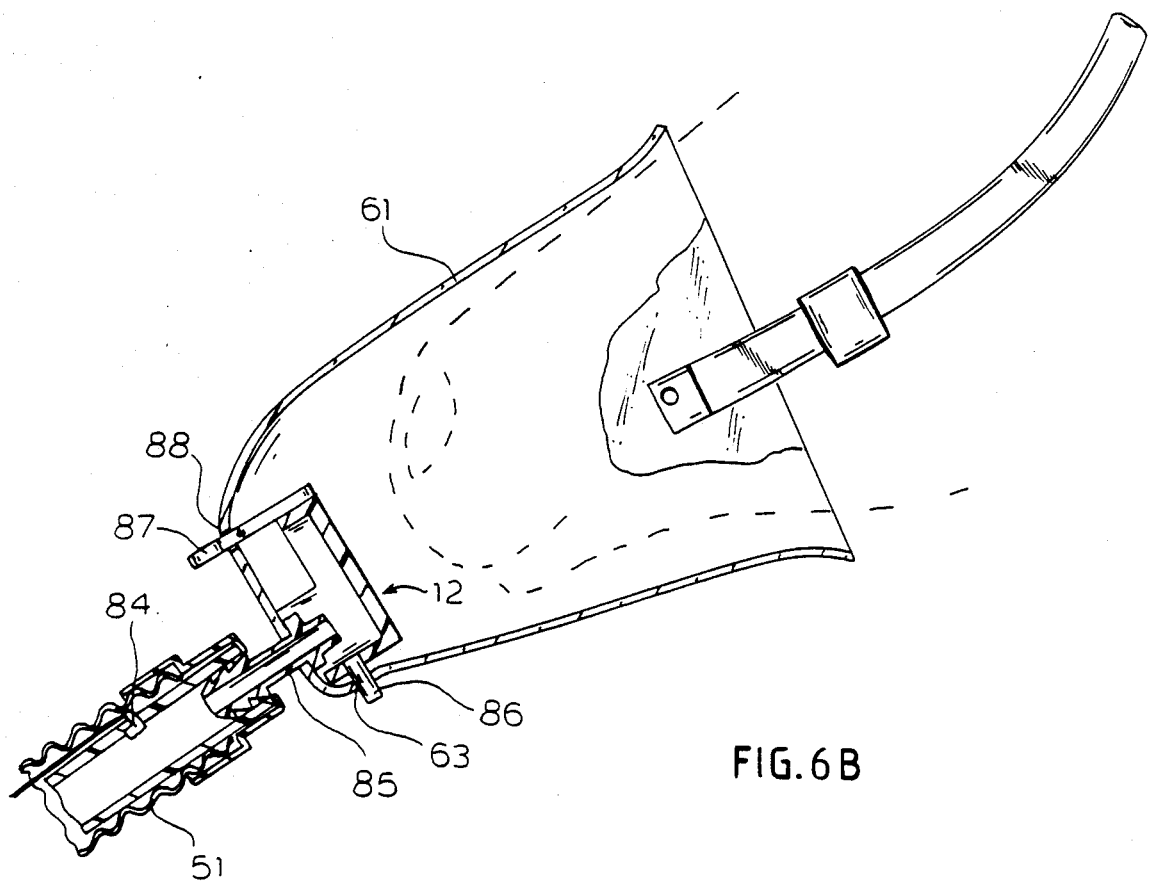
FIG. 6B is a side view of a muzzle mask showing connection to the delivery tube.

FIG. 6B depicts a preferred configuration of a reusable, easily disinfected mask, fabricated with low cost materials (e.g., impregnated paper) for one-time disposable use. Delivery tube 51 connects to bulkhead fitting 85 which is bonded to mask 61. Air exiting the delivery tube impinges directly on diffuser 12 which is held in position by pin 86 and latching retainer 87 which fit into port 63 and slot 88 respectively.

The mask is designed to minimize the formation of aerosols from condensed water in delivery tube 51. It also serves to direct humidified air flow preferentially toward the horse's nostrils to maximize the total amount of water vapor inspired. The snap-in diffuser 12 collects condensate and prevents direct impingement of high velocity humidified air on the horse. Flow channels defined by the mask 61 and diffuser 12 direct the diffused flow toward the nostrils. Excess condensate and secretions from the animal drain from the mask via port 63.

A face or tracheal mask, ventilator, hood, or tent may also be used. The mask may optionally include (not shown) a temperature sensor/indicator to continuously monitor the temperature within the muzzle mask 61 during the administration of therapy.

FIG. 7 depicts an alternate disposable mask 61' which clips directly on the bridle. A J-shaped Tube 90 and U-shaped bracket 89 cooperate to grip flange 91 of mask 61'. Flow from the J-shaped tube is directed against the lower wall of the mask where water droplets are preferentially removed from the air stream by centripetal force as the air flow direction is reversed towards the horse's nostrils. Port 63' allows drainage of condensate and secretions. The entire mask assembly can be attached to the halter by clips and hooks as shown or by independent straps around the horse's head.

An electric circuit board 55 as shown in FIG. 4 is attached to the partition 56. Positioned on the opposite side of the partition are a centrally located transformer 57, a heat sink 58 and two solid state relays 59.

Figure 2:
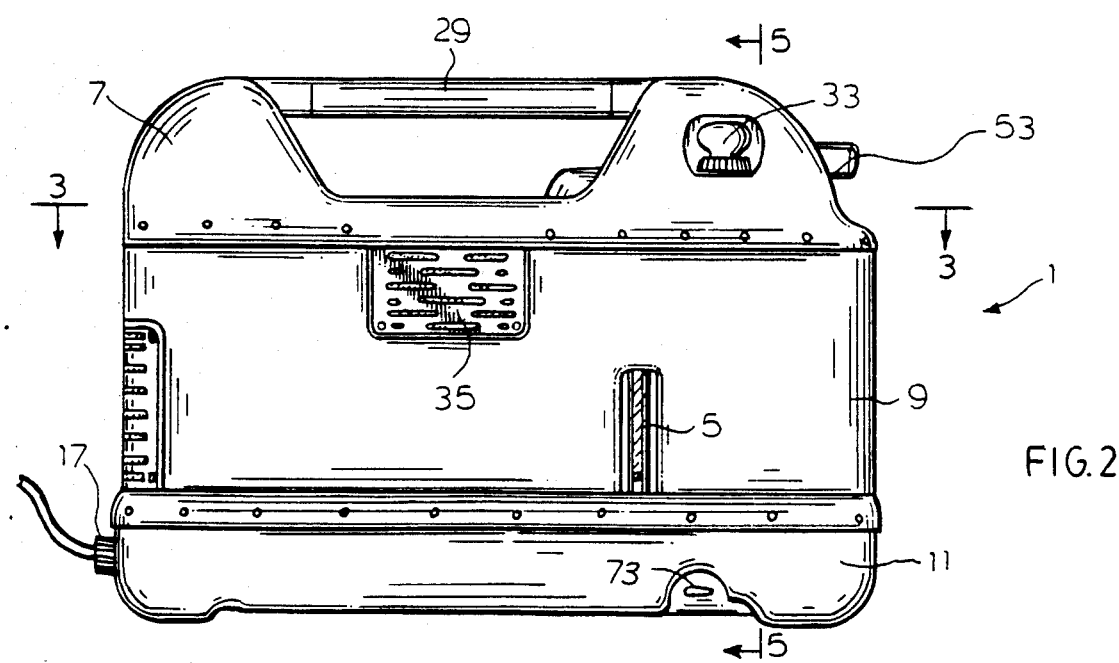
FIG. 2 is a side view of the left side of the portable electric powered humidifier unit.
Figure 3:
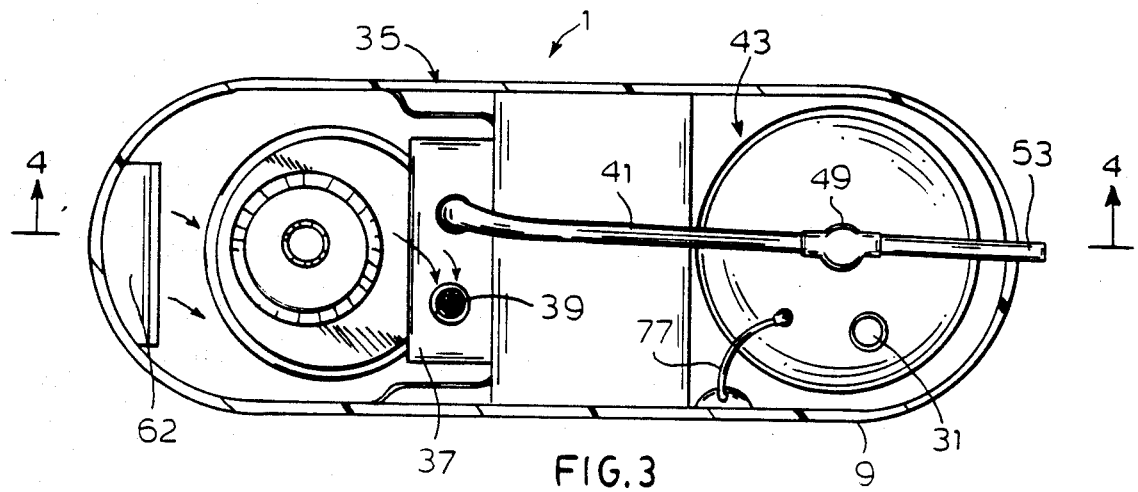
FIG. 3 is a horizontal cut-away showing the internal features of the apparatus.

The exterior of the therapy apparatus of the present invention as shown in FIGS. 2 and 3 is designed for safety. The cabinet 1 includes an upper section 7, a middle section 9, and a lower section 11.

The apparatus is double insulated and grounded. There are no exposed electrical parts. A twist lock electrical plug 17 prevents the animal or the attendant from kicking the plug and breaking the electrical connection. The electrical plug is removable for ease of storage and transportation. The three cabinet sections 7, 9 and 11 are vacuum formed using an acrylo nitrile-butadiene-styrene copolymer, which has good impact resistance and heat resistance under most ambient conditions. This copolymer contributes to the light weight of the apparatus, allowing it to be lifted with relative ease. The apparatus may optionally include integral wheels. However, because it is light weight, this is unnecessary.

The upper section 7 is contoured to prevent water accumulations if the apparatus is left in the elements. For additional safety the control panel 69 is waterproof and positioned in a protected area.

The lower section 11 is water tight since it is formed as one piece. Thus, the device can sit in water without wetting the interior of the device.

The apparatus in its upright position has a low center of gravity for greater stability. This prevents the apparatus from falling over if it is kicked by the animal or the attendant or if it is subjected to a sudden acceleration during transport.

These features are critical because of the environment of actual use. Severe service is expected as the apparatus can be easily transported throughout stables, and can be used to treat several horses on any given day.

An inlet port cap 33 (shown in FIG. 2) maintains container pressure, prevents contamination of the liquid and also prevents spills during transportation. Screen 92 (FIG. 5) filters large particulates from the feed water.

A recess 22 in the upper section 7 (shown in FIG. 1) provides a convenient place for the storage of a disinfectant solution. A handle 29 is centered in the upper section for ease of transporting the cabinet 1.

The control panel 69 has a power switch 52, a test switch 24, a run/dry switch 25, and a digital temperature gauge 23 (not shown). The power switch 52 controls the power to the entire apparatus including heater 45, blower 37, fan 73 and electric control circuitry 55. The run/dry switch 25 is normally placed in the run position. In the dry position, no power is applied to heater 45, but blower 37 continues to operate. The resulting flow of ambient air through the apparatus dries condensate from delivery tube 51. A test switch 24 allows the user to substitute a known resistance for temperature sensor 84. The temperature sensed by sensor 84 is sent on digital temperature gauge 23. When test switch 24 is closed, the gauge reading on 23 indicates whether or not the control is functioning properly. A green light (not shown) may also be on control panel 69 turns on to indicate power is being applied to heater 45. If the temperature at the top of conduit 49 exceeds preset limits a red light (not shown) may also be on control panel 69 turns on to indicate "fault". This temperature is sensed by a sensor (not shown) located at the top of conduit 49. A "fault" signal can be caused by loss of air flow as a result of plumbing failure, blocked conduits, or a failure of blower 37. An elapsed time indicator records the total number of hours the apparatus has been switched on. Either a "refill" or "fault" signal will shut off the power to heater 45.

EXAMPLES

The following examples illustrates the high humidity therapy treatment of large animals as an effective means of preventing and/or healing, reducing, and repairing the tissue damage done to the cells, alveoli, mucousa, nostrils, mucus membranes, nasal passages, broncholi, etc., associated with exercise-induced pulmonary hemorrhage in horses, thoroughbreds and standardbreds, after racing or breezing.

The apparatus of the present invention was started and operated in accordance with the following general procedures on 33 race horses having EIPH. The high-humidity equine device was connected to 115 volt power source. The drain valve of the device was closed and the humidification water reservoir was filled with water via ambient temperature water supply source. The power switch was turned on. The output temperature after 5 to 15 minutes as indicated on the digital temperature meter stabilized from 102° to 108° F. The muzzle mask was connected to the output to bring the dew point temperature to 105° F. at the point of delivery of the saturated vapor gas. The muzzle mask attached to the horses halter. The horses received two-hour treatments, one each of four days preceding the race and the day of the race. Air saturated from 100° F. to 110° F. was administered by muzzle mask at a rate of 300 to 400 liters per minute. The horses were bronchoscoped before treatment and after the race. The results obtained from the 33 known bleeders after begin treated before 60 races are summarized in the table below.

| RESULT OF BRONCHOSCOPIC EXAMINATIONS OF 33 KNOWN BLEEDERS AFTER 60 RACES | | | | |
|---|---|---|---|---|
| Apparatus Used Without Lasix: | Number of Horses Studied | Stopped Bleeding | Less Severe Bleeding | Unchanged Bleeding |
| Saratoga-Meadowlands-Garden State (Harness) | 9 | 4 | 4 | 1 |
| Blue Bonnets (Harness) | 4 | 3 | 1 | 0 |
| Saratoga (Thoroughbred) | 12 | 7 | 3 | 2 |
| Delaware Park | 2 | 0 | 2 | 0 |
| TOTAL | 27 100% | 14 52% | 10 37% | 3 11% |
| Apparatus Used With Lasix | | | | |
| Delaware Park (Thoroughbred) | 6 100% | 2 33% | 2 33% | 2 33% |

Of the 27 horses treated with the apparatus without Lasix, 14 (52%) stopped bleeding, 10 (37%) bled less and only 3 (11%) showed no change. Of the six horses that were known to bleed through Lasix, 2 (33%) stopped bleeding, 2 (33%) showed no change. Overall, 85% of the horses treated bled less and no adverse effects were observed.

In the EIPH Study with the apparatus of the invention, each of the 19 trainers involved were asked to rate their horse's racing performance after treatments: 65% of the races were rated as improved. Many trainers commented that the horse's recovery time after a race was markedly improved: less blowing, and back to feed and water in a shorter period of time. At least 9 of the 33 horses turned in the best performances of their careers. The results are reported on the table below.

| RACING RESULTS OF 33 KNOWN BLEEDERS BEFORE AND AFTER TREATMENTS | | | | |
|---|---|---|---|---|
| Starts | Win | Place | Show | |
| 3 Races before treatment: | | | | |
| 90 | 10 10% | 10 10% | 8 8% | TOTAL 28% |
| Races after treatment: | | | | |
| 93 | 13 14% | 17 18% | 9 10% | TOTAL 42% |

As you can see from the above chart, the win ratio for these 33 horses increased from 10 to 14% after treatment and the Win, Place, Show average increased from 28% to 42%. This is especially noteworthy considering that all 33 horses had exercise-induced pulmonary hemorrhage (EIPH) before treatment.

From an analysis of changes in speed-rating of horses, it has determined that the two-hour treatments pulled mucus and other contaminants, such as racetrack dust, from the horses lungs and permitted them to breathe more freely. As a result the horses as a group ran faster. The treated horses reduced their normalized time for a mile by 1.87 seconds (approximately 10 lengths).

What is claimed is:

1. A veterinary method useful for the therapeutic treatment of an animal respiratory tract comprising the step of delivering to the animal's respiratory tract a substantially sterile humidified vapor-phase stream of gas at a dew point temperature which is greater than the normal body temperature of the animal at a rate in excess of 60 liters per minute to condition the animal's respiratory, pulmonary and cardiovascular system.

2. The method of claim 1 further comprising the step of adding a sedating agent to the stream of gas thereby preventing the dehydration of respiratory and pulmonary airways and preventing water loss from the airways.

3. The method of claim 1, wherein the conditioning provided by the step of delivering the humidified stream of gas comprises increasing the peripheral blood circulation of the animal to warm-up without unnecessarily depleting energy and oxygen reserves.

4. The method of claim 1 wherein the step of delivering the humidified stream of gas further comprises delivering the stream of gas to an animal suffering from bronchitis to condition the animal's bronchi wherein the stream of gas deposits water to soothe inflamed tissue, thereby preventing water loss from the animal's respiratory tract, and allowing the animal to breathe more freely.

5. The method of claim 1, wherein the step of delivering the humidified stream of gas further comprises delivering the stream of gas to an animal suffering from a sinus infection to condition the animal's sinus cavities wherein the stream of gas promotes opening and draining, thereby increasing the blood flow in the infected sinus to promote healing.

6. The method of claim 1, wherein the step of delivering the humidified stream of gas further comprises filtering the stream of gas and delivering the stream of gas to an animal suffering from allergies, wherein the stream of gas deposits water, thereby thinning the mucous blanket, and promoting the removal of irritants from the respiratory system.

7. The method of claim 1, wherein the step of delivering the humidified stream of gas further comprises delivering the stream of gas to an animal suffering from exercised-induced pulmonary hemorrhage to condition the animal's respiratory tract, wherein the stream of gas deposits water, thereby thinning the mucous blanket, dissolving mucous plugs, and promoting mucocilliary clearance.

8. The method of claim 1, wherein the step of delivering the humidified stream of gas further comprises delivering the stream of gas to an animal suffering from pneumonia to condition the animal's lungs wherein the stream of gas promotes mucocilliary clearance of fluids, thereby increasing the blood flow in the pulmonary system.

9. The method of claim 1, wherein the step of delivering the humidified steam of gas further comprises delivering the stream of gas to an animal suffering from airway obstructions wherein the stream of gas deposits water on the walls of the respiratory tract, thereby thinning the mucous blanket, dissolving mucous plugs, and promoting mucocilliary clearance.

10. A method for preparing and introducing a humid air stream into an animal's respiratory tract at temperatures greater than the ambient dew temperature useful for the therapeutic treatment of the animal's respiratory, pulmonary, and cardiovascular systems comprising:
   providing a stream of gas;
   heating water to form water vapor; mixing the vapor with the stream of gas to humidify the stream of gas producing a humidified stream of gas at temperatures greater than the ambient dew temperature;
   delivering the humidified stream of gas to the animal's respiratory tract; and
   depositing water on the walls of the respiratory tract to thin the mucous blanket, dissolve the mucous plugs and promote mucocilliary clearance.

11. The method of claim 10, wherein the step of heating water further includes providing a reservoir for the water, dividing the reservoir and heating only a divided portion of the reservoir so that only a small portion of water is heated to form the water vapor.

12. An apparatus for delivering to a veterinary animal's respiratory tract a humidified steam of gas at a dew point temperature greater than the ambient dew point temperature and also at a temperature greater than the normal body temperature of the animal so as to deposit water on the walls of the respiratory tract comprising:
   a container for storing a reservoir of water;
   means for heating the water in the reservoir to cause vapor to form in said container at a dew point temperature greater than the ambient dew point temperature and also at a temperature greater than the normal body temperature;
   a blower means for providing a stream of gas in excess of 60 liters per minute; and
   a conduit means for conveying the stream of gas into contact with the vapor used and for conveying the stream of humidified gas to the respiratory tract of the animal.

13. The apparatus of claim 12 which further comprises a sequestering means to sequester a portion of the water to be preferentially heated thereby decreasing the delay time from the time the heating means is activated until the vapor forms.

14. The apparatus of claim 13 in which said conduit means further comprises:
   a first conduit in fluid communication with said blower means for conveying a stream of gas away from said blower means;
   a second conduit in fluid communication with said container and the exit end of said first conduit for conveying vapor from said container to the exit end of said first conduit; and
   a third conduit connected at one end to the exit ends of said first and said second conduit and the other end adapted for connection to the animal for conveying the humidified steam of gas to the animal.

15. The apparatus of claim 14 in which said sequestering means comprises:
   a divider means in said container for dividing said container into an inner and outer chamber, said divider means sequestering an inner reservoir which is preferentially heated by said heating means to form the vapor, thus decreasing the delay from the time the heating means is activated until the vapor forms, said divider means permitting only vapor from said inner chamber to flow into said second conduit; and an equilibrium means for equalizing the level of the water and gas pressure between said inner and outer chambers.

16. The apparatus of claim 15 which further comprises a cabinet housing said apparatus of claim 15, including handle means for lifting said cabinet; a recessed filling port communicating with said container, including a cap, said recessed filling port for adding water to said container; and said housing further including a recessed area to hole a bottle.

17. The apparatus of claim 16 which further comprises: a recessed sight means for allowing a visual reading of the water level in said container.

18. The apparatus of claim 17 in which said cabinet is contoured so that water cannot accumulate on the exterior or wet the interior of the cabinet, and the bottom portion of said cabinet is made of one solid piece without holes in it to prevent wetting of the interior of the cabinet.

19. The apparatus of claim 17 in which said cabinet encloses all the electrical parts of said apparatus, and further includes insulating and grounding means, thereby preventing shocking the animal.

20. The apparatus of claim 17 in which said cabinet further comprises a recessed drain means for draining fluid from said container positioned to prevent fluid from spilling on the animal.

21. The apparatus of claim 17 including electrical means to power said blower means and said heating means which further comprises a twist lock electrical plug connected to said blower means and said heating means attached to said cabinet to prevent interruption of electrical connection during use.

22. The apparatus of claim 17 which further comprises, a control panel in said cabinet and switches thereon, said heating means and said blower being responsive to said switches, said control panel having waterproof caps covering the switches to prevent wetting of the interior of said cabinet.

23. The apparatus of claim 17 in which said apparatus has a low center of gravity to minimize the chances of it falling over.

* * * * *